United States Patent [19]

Clifford et al.

[11] Patent Number: 4,539,071

[45] Date of Patent: Sep. 3, 1985

[54] BIOCIDE

[75] Inventors: Richard P. Clifford, South Wirral; Gerrard A. Birchall, Rainford, both of England

[73] Assignee: Dearborn Chemicals Limited, Widnes, England

[21] Appl. No.: 486,007

[22] Filed: Apr. 18, 1983

[30] Foreign Application Priority Data

Apr. 19, 1982 [GB] United Kingdom ............... 8211229

[51] Int. Cl.³ .............................................. D21D 3/00
[52] U.S. Cl. ........................................ 162/161; 71/67; 106/15.05; 106/18.33; 162/158; 210/764
[58] Field of Search ............ 162/161, 158, 175, 181.1, 162/162, 135, 181.4; 210/764; 106/15.05, 18.33; 424/269, 270, 333; 71/67

[56] References Cited

U.S. PATENT DOCUMENTS

| 3,377,275 | 4/1968 | Michalski et al. | 210/764 |
| 4,105,431 | 8/1978 | Lewis et al. | 162/161 |

FOREIGN PATENT DOCUMENTS

| 561523 | 8/1958 | Canada | 210/764 |
| 884541 | 12/1961 | United Kingdom | 162/161 |

OTHER PUBLICATIONS

Richardson, "Cooling-Water System Biofouling", *Chemical Engineering*, pp. 103, 104.
Deegan et al., Research Disclosure 19006, (Feb. 1980).

Primary Examiner—Peter Chin
Attorney, Agent, or Firm—Mark T. Collins

[57] ABSTRACT

This invention relates to the elimination of bacterial deposits in cooling water systems and in water systems used in paper making. This is achieved by using a combination of glutaraldehyde and isothiazolone.

21 Claims, No Drawings

BIOCIDE

This invention relates to the treatment of cooling water systems and of water systems used in paper pulping.

In industrial cooling water systems, for instance in industrial cooling towers, the water used is not, of course, sterile with the result that bacteria accumulate in the system and this quite commonly gives rise to a slimy deposit on the surfaces of the system which come into direct contact with the cooling water. A similar situation applies in paper making; slime can deposit on any of the surfaces with which the water comes into contact including the paper pulping bath on the paper web and in the recirculating back water pipework. A large variety of different treating agents have been used for the purposes of killing these bacteria and/or inhibiting slime formation. These chemicals include quaternary ammonium compounds, amines, isothiazolones, chlorine, phenols, including chlorinated phenols, chlorine-release agents, methylene-bis(thiocyanates), certain aldehydes and tin compounds.

It will, of course, be appreciated that the nature of the bacteria present in the system will vary and biocides which are suitable for use in some cooling water systems may well be inappropriate for use in other aqueous applications and vice versa.

As indicated above, one of the materials used in such systems are the isothiazolones. These are, however, relatively expensive materials. It has now surprisingly been found, according to the present invention, that glutaraldehyde in combination with isothiazolone produces a synergistic effect such that less of both materials is required in the combination to inhibit growth of the bacteria normally found in the water and also of the slime which can be deposited from such water than is the case when using each material separately. Accordingly, the present invention provides a method for the treatment of a cooling water system or of a water system used in paper making which comprises adding to the water, either directly or indirectly, glutaraldehyde and isothiazolone.

The isothiazolones used in the present invention are, in general, those having the formula:

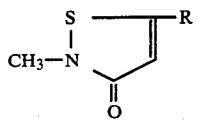

wherein R represents hydrogen or chlorine. A blend of these two isothiazolones is commercially available, the weight ratio of the chlorosubstituted compound to the unsubstituted compound being about 2.66:1.

Although it will normally be more convenient to add the two active ingredients as a mixture it is, of course, possible to add them to the water separately.

In general, the weight ratio of isothiazolone to glutaraldehyde will vary from 1:1 to 1:10, the preferred ratio being 1:3 to 1:5, especially about 1:4.

If the two ingredients are added as a mixture this will usually take the form of an aqueous solution. If desired, a stabilising agent to promote the stability of the isothiazolone on storage can be incorporated, such as cupric nitrate, for example as a 0.2% by weight solution. This is, in addition, to the magnesium chloride (typically 9%) and magnesium nitrate (typically 15%) which is often present in commercially available isothiazolones.

The product mixture will normally contain from about 1 to 15% by weight active ingredient, with the preferred concentration being 7.5 to 12.5% by weight, especially about 9.5%; this composition, with the preferred 1:4 weight ratio of components, can be made up from 12% by weight of isothiazolone (15% active content) and 15% by weight of glutaraldehyde (50% active content).

The precise concentration of use of the biocide will, of course, vary depending on the nature and amount of the bacteria present but, clearly, an amount effective to control the bacteria present should be used. With the preferred concentration in the product mixture one typically should use 25 to 500 ppm of product i.e. 25 to 500 mg of product, per liter of water, corresponding to roughly, 0.45 to 9 ppm of isothiazolone and 1.67 to 33.4 ppm of glutaraldehyde. In general at least 0.05 ppm up to, say, 1000 ppm, in particular 0.25 to 50 ppm, of isothiazolone and at least 0.2 ppm up to, say, 4000 ppm, in particular 1 to 200 ppm, of glutaraldehyde should be used.

In paper making the glutaraldehyde and isothiazolone may be added to the water directly, for example directly to the paper pulping bath or to the recirculating back water, or indirectly, for example to a holding tank containing, generally moist, pulp or along with one or more chemical additives used in paper making. Such additives include starch, for example potato or corn starch, titanium dioxide, a de-foamer such as a fatty acid alcohol, a size, for example a rosin size based on abietic acid, a neutral size based on alkyl ketene dimer or a succinic acid anhydride based size, a wet strength resin such as, if neutral, an epichlorohydrin polyamide or, if acid, a melamine- or urea-formaldehyde resin, various polymers used as dispersants or retention aids such as polyacrylates, polymethacrylates, polyamides and polyacrylamides, clay, chalk, fillers such as carboxymethylcellulose, polyvinyl alcohol and optical brightening agents.

The following Examples illustrate the efficacy of the use of the combination of glutaraldehyde and isothiazolone as compared with the use of the individual ingredients alone. The samples listed below are real samples taken from commercial plants, the reference to "water" being to samples of water taken from the bulk of the system while the reference to "slime" refer to material containing microbiologically active material taken from surfaces in contact with the cooling water. The figures given show the concentrations needed to inhibit bacterial growth as determined by examination using agar plates at the indicated temperature.

| Sample A - Water at 37° C. | |
|---|---|
| (a) Concentration of Isothiazolone in mixture | 0.94 ppm |
| Concentration of Glutaraldehyde in mixture | 3.86 ppm |
| (b) Concentration of Isothiazolone alone | 2.50 ppm |
| (c) Concentration of Glutaraldehyde alone | >20.00 ppm |
| Sample B - Slime at 37° C. | |
| (a) Concentration of Isothiazolone in mixture | 1.88 ppm |
| Concentration of Glutaraldehyde in mixture | 7.52 ppm |
| (b) Concentration of Isothiazolone alone | >5.00 ppm |
| (c) Concentration of Glutaraldehyde alone | 40.00 ppm |
| Sample C - Slime at 37° C. | |
| (a) Concentration of Isothiazolone in mixture | ≦0.47 ppm |
| Concentration of Glutaraldehyde in mixture | ≦1.88 ppm |
| (b) Concentration of Isothiazolone alone | 1.25 ppm |

-continued

| | | |
|---|---|---|
| (c) | Concentration of Glutaraldehyde alone | >40.00 ppm |
| | Sample D - Slime at 20/22° C. | |
| (a) | Concentration of Isothiazolone in mixture | ≦0.47 ppm |
| | Concentration of Glutaraldehyde in mixture | ≦1.88 ppm |
| (b) | Concentration of Isothiazolone alone | 3.86 ppm |
| (c) | Concentration of Glutaraldehyde alone | >40.00 ppm |
| | Sample E - Slime at 37° C. | |
| (a) | Concentration of Isothiazolone in mixture | 3.76 ppm |
| | Concentration of Glutaraldehyde in mixture | 15.04 ppm |
| (b) | Concentration of Isothiazolone alone | >5.00 ppm |
| (c) | Concentration of Glutaraldehyde alone | >40.00 ppm |

Bearing in mind that glutaraldehyde is a much cheaper chemical than isothiazolone, it can be seen that the use of the combination as in the present invention is cheaper than the use of either ingredient alone for the same bactericidal and slimicidal action.

Further Examples illustrating the present invention are given below.

EXAMPLES COMPARING 1:4 AND 1:11 RATIO OF ISOTHIAZOLONE TO GLUTARALDEHYDE

Two biocide blends were prepared. Both of these contained the commercially available mixture of isothiazolones referred to in Examples reported earlier and glutaraldehyde. One of these blends contained isothiazolones and glutaraldehyde in the ratio of 1:4 by weight (Blend A) and the other contained the same components in the ratio 1:11 by weight (Blend B). Both blends were prepared such as to contain the same total concentration of biocide.

| | Isothiazolones | Glutaraldehyde | Ratio of biocides | Total conc$^n$ of biocides |
|---|---|---|---|---|
| A | 1.875% | 7.5% | 1:4 | 9.375% |
| B | 0.775% | 8.6% | 1:11 | 9.375% |

These two blends were then added at concentrations of 25 ppm, 50 ppm, 100 ppm and 200 ppm to three mixed-culture water samples at ambient temperature taken from industrial cooling systems. Aliquots of these samples were removed after various times and incubated in nutrient agar at 22° C. for 3 days. The total counts were measured, and the percentage of bacteria killed calculated by reference to an untreated control.

| Example | Biocide | Conc$^n$ (ppm) | Bacteria killed (%) in 1 hour | 2 hours | 4 hours | 6 hours | 24 hours |
|---|---|---|---|---|---|---|---|
| 1 | A | 25 | 37% | 60% | 76% | 99% | — |
| | | 50 | 58% | 83% | 100% | 100% | — |
| | | 100 | 79% | 100% | 100% | 100% | — |
| | | 200 | 100% | 100% | 100% | 100% | — |
| 1 | B | 25 | 27% | 42% | 66% | 83% | — |
| | | 50 | 41% | 74% | 82% | 98% | — |
| | | 100 | 66% | 100% | 100% | 100% | — |
| | | 200 | 100% | 100% | 100% | 100% | — |
| 2 | A | 25 | 46% | 63% | 79% | 94% | — |
| | | 50 | 65% | 83% | 99% | 100% | — |
| | | 100 | 98% | 100% | 100% | 100% | — |
| | | 200 | 100% | 100% | 100% | 100% | — |
| 2 | B | 25 | 33% | 47% | 68% | 81% | — |
| | | 50 | 51% | 66% | 78% | 96% | — |
| | | 100 | 79% | 84% | 93% | 100% | — |
| | | 200 | 96% | 98% | 100% | 100% | — |
| 3 | A | 25 | — | 13% | 17% | 30% | 86% |
| | | 50 | — | 19% | 53% | 95% | 91% |
| | | 100 | — | 29% | 97% | 100% | 94% |
| | | 200 | — | 97% | 100% | 100% | 97% |
| 3 | B | 25 | — | 1% | 4% | 28% | 92% |
| | | 50 | — | 2% | 24% | 92% | 97% |
| | | 100 | — | 2% | 55% | 97% | 97% |
| | | 200 | — | 10% | 97% | 99% | 97% |

It will be noted that the results obtained using Blend A (containing isothiazolones and glutaraldehyde in the ratio 1:4) are significantly better than those obtained using Blend B (containing isothiazolones and glutaraldehyde in the ratio 1:11).

EXAMPLES OF THE USE OF THE BIOCIDE COMBINATION ON SAMPLES FROM PULP AND PAPER INDUSTRY

The effect of the biocide combination was evaluated on two samples from the pulp and paper industry. Sample 1 was of a recirculating back water, and Sample 2 was a paper pulp slurry. The two biocides evaluated were biocide A, which contained 1.875% of the isothiazolone mixture, and 7.5% glutaraldehyde, and biocide B which contained 2.5% of the isothiazolone mixture. The samples were treated at ambient temperature with concentrations of 25 ppm, 50 ppm, 100 ppm, and 200 ppm of these two biocides. Aliquots of these samples were removed after various times and incubated in nutrient agar at 22° C. for 3 days. The total counts were measured, and the percentage of bacteria killed calculated by reference to an untreated control.

| Sample | Biocide | Conc$^n$ (ppm) | Bacteria killed (%) in 2 Hours | 4 Hours | 6 Hours | 24 Hours |
|---|---|---|---|---|---|---|
| 1 | A | 25 | 45% | 58% | — | 95% |
| | | 50 | 58% | 67% | — | 97% |
| | | 100 | 75% | 100% | — | 97% |
| | | 200 | 97% | 100% | — | 100% |
| 1 | B | 25 | 15% | 47% | — | 95% |
| | | 50 | 16% | 55% | — | 96% |
| | | 100 | 20% | 98% | — | 99% |
| | | 200 | 72% | 100% | — | 100% |
| 2 | A | 10 | 70% | — | 73% | 93% |
| | | 20 | 75% | — | 83% | 97% |
| | | 40 | 80% | — | 94% | 100% |
| 2 | B | 10 | <60% | — | <60% | <60% |
| | | 20 | <60% | — | <60% | <60% |
| | | 40 | <60% | — | 91% | 94% |

We claim:

1. A method for the treatment of a cooling water system or of a water system used in paper making to inhibit baterial growth and slime formation which comprises adding to the water glutaraldehyde and isothiazolone in a weight ratio of isothiazolone to glutaraldehyde of from 1:1 to 1:10 in an amount sufficient to control bacterial growth.

2. A method according to claim 1 wherein the isothiazolone has the general formula:

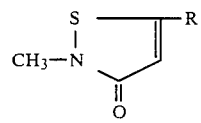

wherein R represents hydrogen or chlorine.

3. A method according to claim 1 wherein the weight ratio of isothiazolone to glutaraldehyde is from 1:3 to 1:5.

4. A method according to claim 3 wherein the weight ratio of isothiazolone to glutaraldehyde is about 1:4.

5. A method according to claim 1 which comprises adding from 0.05 to 1000 ppm of isothiazolone and 0.2 to 4000 ppm of glutaraldehyde.

6. A method according to claim 6 which comprises adding 0.25 to 50 ppm of isothiazolone and 1 to 200 ppm of glutaraldehyde.

7. A method according to claim 1 for the treatment of an industrial cooling water system.

8. A method according to claim 1 which comprises adding the glutaraldehyde and isothiazolone to a recirculating back water used for the paper pulping bath.

9. A method according to claim 1 which comprises adding the glutaraldehyde and isothiazolone directly to the paper pulping bath.

10. A method according to claim 1 which comprises adding the glutaraldehyde and isothiazolone to a holding tank containing moist pulp.

11. A method according to claim 1 which comprises adding the glutaraldehyde and isothiazolone in combination with a chemical additive which is added to the paper pulping bath.

12. A method according to claim 11 wherein the chemical additive is starch, titanium dioxide, a defoamer, a size, a wet strength resin, a dispersant or retention aid, a filler or an optical brightening agent.

13. A biocide composition suitable for addition to an aqueous system which comprises isothiazolone and glutaraldehyde in a weight ratio of isothiazolone to glutaraldehyde of from 1:1 to 1:10.

14. A composition according to claim 13 wherein the weight ratio is from 1:3 to 1:5.

15. A composition according to claim 14 wherein the weight ratio is from 1:4.

16. A composition according to claim 13 which contains from 1 to 15% by weight of isothiazolone and glutaraldehyde, taken together.

17. A composition according to claim 16 which contains from 7.5 to 12.5% by weight of isothiazolone and glutaraldehyde, taken together.

18. A composition according to claim 13 which is in the form of an aqueous solution optionally containing a stabilising agent for the isothiazolone.

19. A composition according to claim 13 which also contains a chemical additive for a paper pulping bath.

20. A composition according to claim 19 wherein the chemical additive is starch, titanium dioxide, a defoamer, a size, a wet strength resin, a dispersant or retention aid, a filler or an optical brightening agent.

21. A composition according to claim 13 which also contains paper pulp.

* * * * *